(12) United States Patent
Takebe et al.

(10) Patent No.: US 7,244,545 B2
(45) Date of Patent: *Jul. 17, 2007

(54) FLUORINATED COMPOUND, FLUOROPOLYMER AND PROCESS FOR ITS PRODUCTION

(75) Inventors: Yoko Takebe, Yokohama (JP); Osamu Yokokoji, Yokohama (JP)

(73) Assignee: Asahi Glass Company, Limited, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 11/412,191

(22) Filed: Apr. 27, 2006

(65) Prior Publication Data

US 2006/0188816 A1 Aug. 24, 2006

Related U.S. Application Data

(63) Continuation of application No. PCT/JP04/16160, filed on Oct. 29, 2004.

(30) Foreign Application Priority Data

| Oct. 31, 2003 | (JP) | ............................. 2003-372654 |
| Feb. 9, 2004 | (JP) | ............................. 2004-032038 |
| Jun. 23, 2004 | (JP) | ............................. 2004-185091 |

(51) Int. Cl.
*G03C 1/73* (2006.01)
*C08F 14/18* (2006.01)
*C07C 33/42* (2006.01)
*C07C 21/19* (2006.01)

(52) U.S. Cl. ............... 430/270.1; 430/907; 430/914; 526/242; 568/843; 568/845; 570/126; 570/131; 570/136

(58) Field of Classification Search ................ None
See application file for complete search history.

(56) References Cited

U.S. PATENT DOCUMENTS

| 6,733,952 | B2 | 5/2004 | Kaneko et al. ............ 430/270.1 |
| 6,815,146 | B2 | 11/2004 | Okada et al. ............ 430/270.1 |
| 6,818,258 | B2 | 11/2004 | Kaneko et al. ............ 427/553 |
| 6,858,692 | B2 | 2/2005 | Kaneko et al. ............ 526/252 |
| 6,916,590 | B2 | 7/2005 | Kaneko et al. ............ 430/270.1 |
| 6,984,704 | B2 | 1/2006 | Kodama et al. ............ 526/250 |
| 7,015,366 | B2 | 3/2006 | Kodama et al. ............ 568/840 |
| 2004/0033439 | A1 | 2/2004 | Kaneko, et al. ............ 430/270.1 |
| 2005/0202345 | A1 | 9/2005 | Kawaguchi et al. | |
| 2006/0135663 | A1 | 6/2006 | Takebe et al. | |
| 2006/0188816 | A1 | 8/2006 | Takebe et al. | |

FOREIGN PATENT DOCUMENTS

| EP | 1 365 290 | 11/2003 |
| JP | 04-189880 | 7/1992 |
| JP | 04-226177 | 8/1992 |
| JP | 06-220232 | 8/1994 |
| WO | 00/17712 | 3/2000 |
| WO | 01/37044 | 5/2001 |
| WO | 01/63362 | 8/2001 |
| WO | 02/064648 | 8/2002 |
| WO | 02/065212 | 8/2002 |
| WO | WO 2005/108446 A1 | 11/2005 |
| WO | WO 2006/011427 A1 | 2/2006 |

OTHER PUBLICATIONS

U.S. Appl. No. 11/336,943, filed Jan. 23, 2006, Takebe, et al.
U.S. Appl. No. 11/593,549, filed Nov. 7, 2006, Eda et al.

*Primary Examiner*—Sin Lee
(74) *Attorney, Agent, or Firm*—Oblon, Spivak, McClelland, Maier & Neustadt, P.C.

(57) ABSTRACT

The present invention provides a fluorinated compound having functional groups in a high concentration so that adequate characteristics of the functional groups can be obtained and having high transparency in a wide wavelength region, a fluoropolymer, and a process for its production.

The present invention provides a fluorinated diene represented by the following formula (1):

$$CF_2=CFCH_2CH(C(R^1)(R^2)(OH))CH_2CH=CH_2 \quad (1)$$

wherein each of $R^1$ and $R^2$ which are independent of each other, is a fluorine atom or a fluoroalkyl group having at most 5 carbon atoms.

15 Claims, No Drawings

FLUORINATED COMPOUND, FLUOROPOLYMER AND PROCESS FOR ITS PRODUCTION

TECHNICAL FIELD

The present invention relates to a novel fluorinated compound, a fluoropolymer and a process for its production.

BACKGROUND ART

As fluoropolymers having functional groups, functional group-containing fluoropolymers are known which are used for fluorinated ion exchange membranes, curable fluorinated resin coating materials, etc. However, they are all basically straight chained polymers, and they are obtainable by copolymerization of a fluoroolefin represented by tetrafluoroethylene with a monomer having a functional group.

Further, a polymer containing functional groups and having fluorinated alicyclic structures in its main chain, is also known. As a method for introducing functional groups to the polymer having fluorinated alicyclic structures in its main chain, a method of utilizing terminal groups of a polymer obtained by polymerization, a method of subjecting a polymer to high temperature treatment to oxidize and decompose side chains or terminals of the polymer to form functional groups, or a method of copolymerizing a monomer having a functional group, if necessary, followed by treatment such as hydrolysis to introduce functional groups, is, for example, known (for example, Patent Documents 1, 2, 3 and 4).

The above-mentioned methods are available as methods for introducing functional groups to a polymer having fluorinated alicyclic structures in its main chain. However, the method for introducing functional groups by treating the terminal groups of the polymer, has a drawback that the functional group concentration is low, and no adequate properties of the functional groups can be obtained. Whereas, by the method for introducing functional groups by copolymerizing a monomer having a functional group, there will be a problem such that if the functional group concentration is increased, the mechanical properties tend to decrease due to a decrease of the glass transition temperature (Tg).

Patent Document 1: JP-A-4-189880
Patent Document 2: JP-A-4-226177
Patent Document 3: JP-A-6-220232
Patent Document 4: WO02/064648

DISCLOSURE OF THE INVENTION

Objects to be Accomplished by the Invention

It is an object of the present invention to provide a fluorinated compound having functional groups in a high concentration so that adequate properties of the functional groups can be obtained and having high transparency in a wide wavelength region, a fluoropolymer and a process for its production. Further, it is an object of the present invention to provide a resist composition which is excellent particularly in transparency for far ultraviolet rays such as KrF or ArF excimer laser or vacuum violet rays such as $F_2$ excimer laser and dry etching properties, as a chemical amplification type resist, and which can form a resist pattern excellent in sensitivity, resolution, dissolution velocity, flatness and the like. Furthermore, it is an object of the present invention to provide a protective film to protect a resist film from an immersion solvent in an immersion lithography process.

Means to Accomplish the Objects

The present invention has been made to accomplish the above objects and provides the following.

The present invention provides a fluorinated diene represented by the following formula (1):

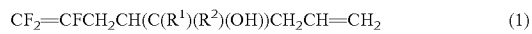

$$CF_2=CFCH_2CH(C(R^1)(R^2)(OH))CH_2CH=CH_2 \qquad (1)$$

wherein each of $R^1$ and $R^2$ which are independent of each other, is a fluorine atom or a fluoroalkyl group having at most 5 carbon atoms.

The present invention provides a fluoropolymer (A) having monomer units formed by cyclopolymerization of the fluorinated diene represented by the above formula (1), and a process for its production.

Further, the present invention provides a composition for a resist protective film, characterized by comprising the fluoropolymer (A) and a solvent for dissolving or dispersing the fluoropolymer (A).

EFFECT OF THE INVENTION

According to the present invention, it is possible to produce a fluoropolymer having alicyclic structures in its main chain and having hydroxyl groups in its side chains. The fluoropolymer obtained by the present invention has high chemical stability and heat resistance. Yet, hydroxyl groups are introduced in the side chains, whereby it is possible to exhibit adequate properties of hydroxyl groups without bringing about a decrease of Tg, which used to be difficult to accomplish with conventional fluoropolymers. Particularly, it has hydroxyl groups having high acidity in the side chains of the cyclic structures, whereby the solubility in an aqueous alkali solution is improved. Further, it has high transparency in a wide wavelength region.

BEST MODE FOR CARRYING OUT THE INVENTION

By the present invention, a fluorinated diene represented by the following formula (1) (hereinafter referred to as the fluorinated diene (1)), a fluoropolymer (A) having monomer units formed by cyclopolymerization of the fluorinated diene (1), and a process for its production can be provided:

$$CF_2=CFCH_2CH(C(R^1)(R^2)(OH))CH_2CH=CH_2 \qquad (1)$$

wherein each of $R^1$ and $R^2$ which are independent of each other, is a fluorine atom or a fluoroalkyl group having at most 5 carbon atoms. Particularly, $R^1$ and/or $R^2$ is preferably a trifluoromethyl group, and both $R^1$ and $R^2$ are most preferably trifluoromethyl groups.

The fluorinated diene of the present invention can be produced by known methods. For example, in the presence of a radical initiator, $CF_2ClCFClI$ is added to a double bond of $CH_2=CHC(R^1)(R^2)OH$ as a starting material to form $CF_2ClCFClCH_2CHIC(R^1)(R^2)OH$, and then $CH_2=CHCH_2MgCl$ is reacted therewith, followed by dechlorination, to obtain the fluorinated diene. By changing $R^1$ and $R^2$, the following various fluorinated dienes (1) can be obtained.

The following compounds may be mentioned as specific examples of the fluorinated diene (1) of the present invention, but the present invention is not limited thereto.

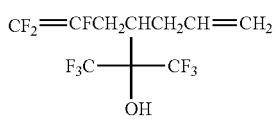
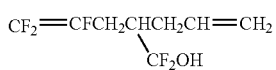
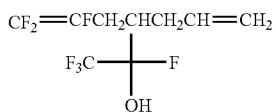
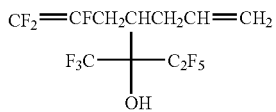
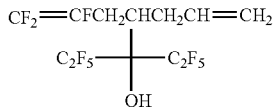
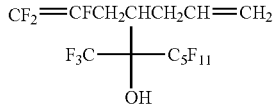
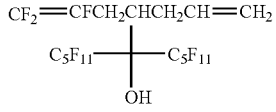

Such a fluorinated diene (1) can be cyclopolymerized under a relatively mild condition, whereby a cyclized polymer having hydroxyl groups in the side chains of the cyclic structures, can be obtained.

By the cyclopolymerization of the fluorinated diene (1), the following monomer units (a) to (c) are considered to be formed, and from the results of the spectroscopic analysis, etc., the fluoropolymer (A) is considered to be a polymer having a structure comprising at least one type of monomer units selected from the group consisting of monomer units (a), monomer units (b) and monomer units (c).

(a)
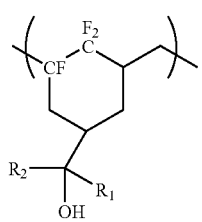

(b)
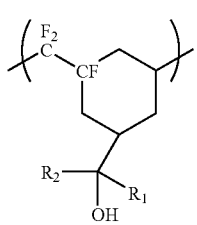

(c)
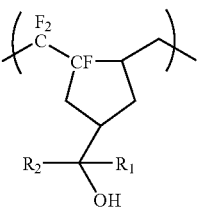

It is preferred that in addition to cyclopolymerized monomer units having the fluorinated diene (1) (hereinafter referred to as the monomer units (1)), the fluoropolymer (A) has monomer units having blocked hydroxyl groups of the monomer units (1) (hereinafter referred to as the blocked monomer units (1)). The proportion of such blocked monomer units (1) is preferably at most 50 mol %, particularly preferably from 15 to 40 mol %, based on the total of the monomer units (1) and the blocked monomer units (1). Here, the "blocked" means that a hydrogen atom of a hydroxyl group is substituted by a blocking group. Specific examples of blocked hydroxyl groups may be —OCH$_3$, —OCF$_3$, —O(t-C$_4$H$_9$), —OCH$_2$OCH$_3$, —OCH$_2$OC$_2$H$_5$, —OCH$_2$OCH$_2$OCH$_3$, —OCH$_2$OCH$_2$CF$_3$, —OCOO(t-C$_4$H$_9$), —OCH(CH$_3$)OC$_2$H$_5$, a 2-tetrahydropyranyloxy group and the following groups.

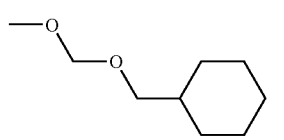
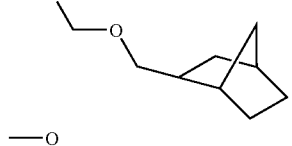
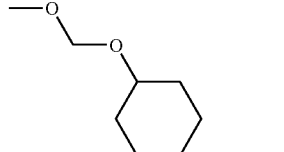
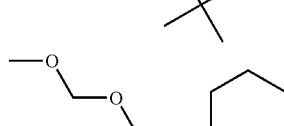

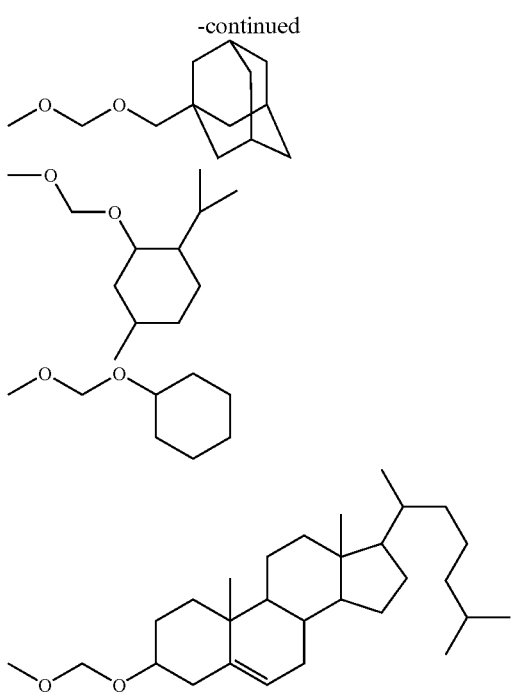

The fluoropolymer (A) having the monomer units (1) and the blocked monomer units (1) can be obtained by copolymerizing a fluorinated diene (1) with a blocked fluorinated diene obtained by blocking a hydroxyl group of a fluorinated diene (1). Further, it can also be obtained by blocking part of hydroxyl groups of the monomer units (1) of the fluoropolymer (A) having such monomer units (1).

In addition to the monomer units (1), the fluoropolymer (A) may further contain monomer units (other than the blocked monomer units (1)) derived from other radical polymerizable monomers within a range not to impair the properties. The proportion of such monomer units derived from the other radical polymerizable monomers is preferably at most 50 mol %, particularly preferably at most 15 mol %.

Such other radical polymerizable monomers may, for example, be an α-olefin such as ethylene, propylene or isobutylene, a fluorinated olefin such as tetrafluoroethylene or hexafluoropropylene, a fluorinated cyclic monomer such as perfluoro(2,2-dimethyl-1,3-dioxol), a cyclopolymerizable perfluorodiene such as perfluoro(butenyl vinyl ether), a cyclopolymerizable hydrofluorodiene such as 1,1,2,3,3-pentafluoro-4-trifluoromethyl-4-hydroxy-1,6-heptadiene or 1,1,2-triluoro-4-[3,3,3-trifluoro-2-hydroxy-2-trifluoromethyl propyl]-1,6-heptadiene, an acryl ester such as methyl acrylate or ethyl methacrylate, a vinyl ester such as vinyl acetate, vinyl benzoate or vinyl adamantate, a vinyl ether such as ethyl vinyl ether or cyclohexyl vinyl ether, a cyclic olefin such as cyclohexene, norbornene or norbornadiene, maleic anhydride, and vinyl chloride.

The fluoropolymer (A) of the present invention can be obtained by homopolymerizing the fluorinated diene (1) or copolymerizing it with other copolymerizable monomers in the presence of a polymerization initiating source. The polymerization initiating source is not particularly limited so long as it is capable of letting the polymerization reaction proceed radically, and it may, for example, be a radical-generating agent, light or ionizing radiation. Particularly, a radical-generating agent is preferred, and such a radical-generating agent may, for example, be a peroxide, an azo compound or a persulfate. Among such radical-generating agents, a peroxide is preferred. As specific peroxides, the following compounds may be mentioned:

$C_6H_5-C(O)O-OC(O)-C_6H_5$ $C_6F_5-C(O)O-OC(O)-C_6F_5$ $C_3F_7-C(O)O-OC(O)-C_3F_7$ $(CH_3)_3C-C(O)O-OC(O)-C(CH_3)_3$ $(CH_3)_2CH-C(O)O-OC(O)-CH(CH_3)_2$ $(CH_3)_3C-C_6H_{10}-C(O)O-OC(O)-C_6H_{10}-C(CH_3)_3$ $(CH_3)_3C-C-C(O)O-OC(O)-O-C(CH_3)_3$ $(CH_3)_2CH-O-C(O)O-OC(O)-O-CH(CH_3)_2$ $(CH_3)_3C-C_6H_{10}-O-C(O)O-OC(O)-O-C_6H_{10}-C(CH_3)_3$ wherein $-C_6H_5$ represents a phenyl group, $-C_6F_5$ a heptafluorophenyl group and $-C_6H_{10}-$ a cyclohexylene group.

The polymerization method is also not particularly limited, and it may, for example, be so-called bulk polymerization wherein a monomer is subjected to polymerization as it is, solution polymerization which is carried out in a fluorohydrocarbon, a chlorohydrocarbon, a fluorochlorohydrocarbon, an alcohol, a hydrocarbon or other organic solvent, which can dissolve or disperse fluorinated diene (1) and other monomers, suspension polymerization which is carried out in an aqueous medium in the presence or absence of a suitable organic solvent, or emulsion polymerization which is carried out by adding an emulsifier to an aqueous medium.

The polymerization temperature and pressure are also not particularly limited, but it is preferred to properly set them taking into consideration various factors such as the boiling point of the monomer, the heating source, removal of the polymerization heat, etc. For example, suitable temperature setting can be carried out between 0° C. and 200° C., and practically suitable temperature setting can be carried out within a range of from room temperature to 100° C. Further, the polymerization pressure may be a reduced pressure or an elevated pressure, and practically, the polymerization can properly be carried out within a range of from normal pressure to about 100 atm, preferably from normal pressure to about 10 atm.

The molecular weight of the fluoropolymer (A) of the present invention is not particularly limited so long as it is uniformly soluble in an organic solvent (C) as described hereinafter and can uniformly be applied on a substrate. However, usually, the number average molecular weight as calculated as polystyrene is appropriately from 1,000 to 100,000, preferably from 2,000 to 30,000. If the number average molecular weight is at least 1,000, it is unlikely that the obtained resist pattern is impaired, the film-remaining rate after development decreases, or the shape stability at the time of pattern heat treatment decreases. Further, if the number average molecular weight is at most 100,000, the coating properties of the resist composition as mentioned below may suitably be maintained, and the development properties may suitably be maintained.

The fluoropolymer (A) of the present invention can be used as a base polymer for photoresists. Namely, it can be used for a resist composition by forming a composition containing the fluoropolymer (A), an acid-generating compound (B) which generates an acid under irradiation with light and an organic solvent (C). Now, a resist composition containing the fluoropolymer (A) as a base polymer (hereinafter referred to as the resist composition (D)) will be explained with reference to a fluoropolymer (A) having the monomer units (1) and the blocked monomer units (1) as a preferred embodiment of the fluoropolymer (A), as an example.

The above acid-generating compound (B) which generates an acid under irradiation with light, generates an acid by exposure. By the acid thus generated, part or all of blocked groups of blocked monomer units (1) in the fluoropolymer (A), is cleaved (deblocked). As a result, the exposed portions will become readily soluble by an alkali developer, whereby a positive resist pattern can be formed by the alkali developer. As such an acid-generating compound (B) which generates an acid under irradiation with light, it is possible to employ an acid-generating compound which is commonly used for a chemical amplification type resist material. Namely, an onium salt, a halogenated compound, a diazoketone compound, a sulfone compound or a sulfonic acid compound may, for example, be mentioned. The following compounds may be mentioned as examples of such an acid-generating compound (B).

The onium salt may, for example, be an iodonium salt, a sulfonium salt, a phosphonium salt, a diazonium salt or a pyridinium salt. Specific examples of a preferred onium salt include diphenyliodonium triflate, diphenyliodoniumpyrene sulfonate, diphenyliodoniumdodecylbenzene sulfonate, bis(4-tert-butylphenyl)iodonium triflate, bis(4-tert-butylphenyl)iodonium dodecylbenzene sulfonate, triphenylsulfonium triflate, triphenylsulfonium nonanate, triphenylsulfoniumperfluorooctane sulfonate, triphenylsulfonium hexafluoroantimonate, 1-(naphthylacetomethyl)thiolanium triflate, cyclohexylmethyl(2-oxocyclohexyl)sulfonium triflate, dicyclohexyl(2-oxocyclohexyl)sulfonium triflate, dimethyl(4-hydroxynaphthyl)sulfonium tosylate, dimethyl(4-hydroxynaphthyl)sulfonium dodecylbenzene sulfonate, dimethyl(4-hydroxynaphthyl)sulfonium naphthalene sulfonate, triphenylsulfonium camphor sulfonate and (4-hydroxyphenyl)benzylmethylsulfonium toluene sulfonate.

The halogenated compound may, for example, be a haloalkyl group-containing hydrocarbon compound or a haloalkyl group-containing heterocyclic compound. Specifically, it may, for example, be a (trichloromethyl)-s-triazine derivative such as phenyl-bis(trichloromethyl)-s-triazine, methoxyphenyl-bis(trichloromethyl)-s-triazine or naphthyl-bis(trichloromethyl)-s-triazine, or 1,1-bis(4-chlorophenyl)-2,2,2-trichloroethane.

The sulfone compound may, for example, be β-ketosulfone, β-sulfonylsulfone or an α-diazo compound of such a compound. Specifically, it may, for example, be 4-trisphenacylsulfone, mesitylphenacylsulfone or bis(phenylsulfonyl)methane. The sulfonic acid compound may, for example, be an alkylsulfonic acid ester, an alkylsulfonic acid imide, a haloalkylsulfonic acid ester, an arylsulfonic acid ester or an iminosulfonate. Specifically, it may, for example, be benzoine tosylate or 1,8-naphthalene dicarboxylic acid imide triflate. Such acid-generating compounds (B) may be used alone or in combination as a mixture of two or more of them.

The organic solvent (C) of the present invention is not particularly limited so long as it is capable of dissolving both components of the fluoropolymer (A) and the acid-generating compound (B) It may, for example, be an alcohol such as methyl alcohol or ethyl alcohol, a ketone such as acetone, methyl isobutyl ketone or cyclohexanone, an acetate such as ethyl acetate or butyl acetate, an aromatic hydrocarbon such as toluene or xylene, a glycol monoalkyl ether such as propylene glycol monomethyl ether or propylene glycol monoethyl ether, or a glycol monoalkyl ether ester such as propylene glycol monomethyl ether acetate or carbitol acetate.

The proportions of the respective components in the resist composition (D) are usually such that the acid-generating compound (B) is from 0.1 to 20 parts by mass and the organic solvent (C) is from 50 to 2,000 parts by mass, per 100 parts by mass of the fluoropolymer (A). Preferably, the acid-generating compound (B) is from 0.1 to 10 parts by mass and the organic solvent (C) is from 100 to 1,000 parts by mass, per 100 parts by mass of the fluoropolymer (A).

If the amount of the acid-generating compound (B) is at least 0.1 part by mass, sufficient sensitivity and developability can be provided, and if it is at most 10 parts by mass, sufficient transparency to radiation can be maintained, whereby a more accurate resist pattern can be obtained.

In the resist composition (D), an acid-cleavable additive to improve the pattern contrast, a surfactant to improve the coating property, a nitrogen-containing basic compound to adjust the acid-generating pattern, an adhesion-assisting agent to improve the adhesion to a substrate, a storage stabilizer to enhance the storage stability of the composition, or the like may be optionally incorporated. Further, the resist composition of the present invention is preferably employed in such a manner that the respective components are uniformly mixed, followed by filtration by means of a filter of from 0.1 to 2 µm.

The resist composition (D) is applied on a substrate such as a silicon wafer, followed by drying to form a resist film. As the coating method, spin coating, cast coating or roll coating may, for example, be employed. The formed resist film will be irradiated with light through a mask having a pattern drawn thereon, followed by development treatment to form the pattern.

The light beams for the irradiation may, for example, be ultraviolet rays such as g-line having a wavelength of 436 nm, or i-line having a wavelength of 365 nm, or far ultraviolet rays or vacuum ultraviolet rays, such as KrF excimer laser having a wavelength of 248 nm, ArF excimer laser having a wavelength of 193 nm or $F_2$ excimer laser having a wavelength of 157 nm. The resist composition (D) is a resist composition useful particularly for an application where ultraviolet rays having a wavelength of at most 250 nm, especially ultraviolet rays having a wavelength of at most 200 nm (such as ArF excimer laser or $F_2$ excimer laser), are used as the light source.

As the development treatment solution, various alkali aqueous solutions may be employed. As such an alkali, sodium hydroxide, potassium hydroxide, ammonium hydroxide, tetramethyl ammonium hydroxide or triethylamine may, for example, be mentioned.

Further, the fluoropolymer (A) of the present invention is insoluble in water and soluble in a developer, and therefore it can be used also as a base polymer for a resist protective film. A solvent (E) for dissolving or dispersing the fluoropolymer (A) is mixed with the fluoropolymer (A), and the mixture is then applied on a resist film, followed by drying to form a resist protective film. As the coating method, spin coating, cast coating or roll coating may, for example, be employed. The formed resist protective film will be irradiated with light through a mask having a pattern drawn thereon, followed by development treatment to remove the resist protective film and to form the pattern of the resist film.

The above solvent (E) is not particularly limited so long as it is capable of dissolving or dispersing the fluoropolymer (A), and is preferably one which is capable of dissolving it. Further, it is preferably a solvent having little influence on a resist material because it is applied on a resist film. The solvent (E) may, for example, be an alcohol such as methyl alcohol or ethyl alcohol, a ketone such as acetone, methyl isobutyl ketone or cyclohexanone, and acetate such as ethyl acetate or butyl acetate, an aromatic hydrocarbon such as toluene or xylene, a glycol monoalkyl ether such as propylene glycol monomethyl ether or propylene glycol monoethyl ether, or a glycol monoalkyl ether ester such as propylene glycol monomethyl ether acetate or carbitol acetate or a fluorine solvent. It may be a mixture of the above solvents, or in a case where it is a water-soluble organic solvent, it may be a mixture with water.

It is preferred that the proportion of the solvent (E) is from 50 to 2,000 parts by mass, per 100 parts by mass of the fluoropolymer (A). Preferably, the solvent (E) is from 100 to 1,000 parts by mass, per 100 parts by mass of the fluoropolymer (A). It is preferred that the fluoropolymer (A) and the solvent (E) are uniformly mixed, followed by filtration with use of a filter of from 0.1 to 2 µm.

In addition to the fluoropolymer (A) and the solvent (E), other components may be contained therein. Such a resist protective film is preferably used in an immersion lithography process used for improvement of resolution. Further, it is most preferably used in an immersion lithography process using water.

The light for the irradiation may, for example, be ultraviolet rays such as g-line having a wavelength of 436 nm or i-line having a wavelength of 365 nm, or far ultraviolet rays or vacuum ultraviolet rays, such as KrF excimer laser having a wavelength of 248 nm, ArF excimer laser having a wavelength of 193 nm or $F_2$ excimer laser having a wavelength of 157 nm. The fluoropolymer (A) of the present invention can be used as a base polymer for a resist protective film useful particularly for an application where ultraviolet rays having a wavelength of at most 250 nm, especially ultraviolet rays having a wavelength of at most 200 nm (such as ArF excimer laser or $F_2$ excimer laser), are used as the light source.

EXAMPLES

Now, the present invention will be described in detail with reference to Examples, but it should be understood that the present invention is by no means restricted thereto.

Abbreviations used in the following Examples are as follows.

THF; tetrahydrofuran, BPO; benzoylperoxide, PFBPO; perfluorobenzoylperoxide, PFB; perfluorobutyrylperoxide, PSt; polystyrene, R225; dichloropentafluoropropane (solvent).

Example 1

Preparation of $CF_2=CFCH_2CH(C(CF_3)_2OH)CH_2CH=CH_2$

Into a 1 L (liter) glass reactor, 500 g of $CF_2ClCFClI$, 344 g of $CH_2=CHC(CF_3)_2OH$ and 32.6 g of BPO were put and heated to 95° C. for 71 hours. The reaction crude liquid was distilled under reduced pressure to obtain 544 g of $CF_2ClCFClCH_2CHI(C(CF_3)_2OH)$ (55-58° C./0.2 kPa).

Into a 5 L glass reactor, 344 g of the above prepared $CF_2ClFClCH_2CHI(C(CF_3)_2OH)$ and 1.7 L of dehydrated THF were put and cooled to −70° C. 1.8 L of a 2M-THF solution of $CH_2=CHCH_2MgCl$ was dropwise added thereto over a period of 4 hours.

After the temperature was raised to 0° C. and stirring was carried out for 16 hours, 1.6 L of an aqueous saturated ammonium chloride solution was added thereto, and the temperature was raised to room temperature. The reaction solution was subjected to liquid separation, and the organic layer was concentrated by an evaporator and then distilled under reduced pressure to obtain 287 g of $CF_2ClCFClCH_2CH(C(CF_3)_2OH)CH_2CH=CH_2$ (62-66° C./0.2 kPa). Into a 1 L glass reactor, 97 g of zinc and 300 g of water were put and heated to 90° C. Then, 287 g of the above prepared $CF_2ClCFClCH_2CH(C(CF_3)_2OH)CH_2CH=CH_2$ was dropwise added thereto, followed by stirring for 24 hours. After 70 mL of hydrochloric acid was dropwise added to the reaction solution and stirring was carried out for 2 hours, the reaction solution was filtrated and subjected to liquid separation, and then distilled under reduced pressure to obtain 115 g of $CF_2=CFCH_2CH(C(CF_3)_2OH)CH_2CH=CH_2$ (53-54° C./kPa).

NMR Spectra $^1$H-NMR (399.8 MHz, solvent: $CDCl_3$, standard: tetramethylsilane) δ (ppm): 2.53 (m, 5H), 3.49 (m, 1H), 5.15 (m, 2H), 5.79 (m, 2H). $^{19}$F-NMR (376.2 MHz, solvent: $CDCl_3$, standard: $CFCl_3$) δ (ppm): −73.6 (m, 6F), −104.1 (m, 1F), −123.1 (m, 1F), −175.4 (m, 1F).

Example 2

5 g of the monomer obtained in Example 1 was charged into a pressure resistant reactor made of glass and having an internal capacity of 30 mL. Then, 0.13 g of PFBPO was added as a polymerization initiator. The interior of the system was freeze-deaerated, and then the reactor was sealed, followed by polymerization for 19 hours in a constant temperature shaking bath (70° C.). After the polymerization, the reaction solution was diluted with R225 and was dropped into hexane to reprecipitate the polymer, followed by vacuum drying at 115° C. for 18 hours. As a result, 3.32 g of a non-crystalline polymer having fluorinated cyclic structures in its main chain (hereinafter referred to as the polymer 1A) was obtained. The molecular weight measured by GPC employing THF as a solvent and calculated as PSt, was such that the number average molecular weight (Mn) was 26,300, the weight average molecular weight (Mw) was 56,300, and Mw/Mn=2.14. Tg measured by the differential scanning calorimetery (DSC) was 124° C., and the polymer was a white powder at room temperature. The polymer obtained was soluble in acetone, THF, ethylacetate, methanol and R225, and was insoluble in hexane.

By $^{19}$F-NMR and $^1$H-NMR, it was confirmed to be a cyclized polymer having the following monomer units (d), (e) and (f).

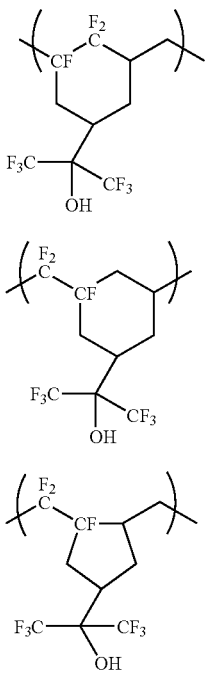

(d)

(e)

(f)

Example 3

4 g of the monomer obtained in Example 1 and 2.2 g of ethyl acetate were charged into a pressure resistant reactor made of glass and having an internal capacity of 30 mL. Then, 6.23 g of a 3 wt % solution of PFB in R225 was added as a polymerization initiator. The interior of the system was freeze-deaerated, and then the reactor was sealed, followed by polymerization for 41 hours in a constant temperature shaking bath (20° C.). After the polymerization, the reaction solution was dropped into hexane to reprecipitate the polymer, followed by vacuum drying at 90° C. for 21 hours. As a result, 1.33 g of a non-crystalline polymer having fluorinated cyclic structures in its main chain (hereinafter referred to as the polymer 2A), was obtained. The molecular weight measured by GPC employing THF as a solvent and calculated as PSt, was such that the number average molecular weight (Mn) was 15,600, and the weight average molecular weight (Mw) was 25,100, and Mw/Mn=1.61. Tg measured by the differential scanning calorimetery (DSC) was 118° C., and the polymer was a white powder at room temperature. The polymer obtained was soluble in acetone, THF, methanol and R225.

Example 4

10 g of the monomer obtained in Example 1 was charged into a pressure resistant reactor made of glass and having an internal capacity of 50 mL. Then, 40.6 g of a 3 wt % solution of PFB in R225 was added as a polymerization initiator. The interior of the system was freeze-deaerated, and then the reactor was sealed, followed by polymerization for 18.5 hours in a constant temperature shaking bath (20° C.). After the polymerization, the reaction solution was diluted with R225 and was dropped into hexane to reprecipitate the polymer, followed by vacuum drying at 120° C. for 15 hours. As a result, 8.5 g of a non-crystalline polymer having fluorinated cyclic structures in its main chain (hereinafter referred to as the polymer 3A), was obtained. The molecular weight measured by GPC employing THF as a solvent and calculated as PSt, was such that the number average molecular weight (Mn) was 15,500, and the weight average molecular weight (Mw) was 26,000, and Mw/Mn=1.69. Tg measured by the differential scanning calorimetery (DSC) was 117° C., and the polymer was a white powder at room temperature. The polymer obtained was soluble in acetone, THF, methanol and R225.

Example 5

2 g of the monomer obtained in Example 1 and 1.6 g of dioxane were charged into a pressure resistant reactor made of glass and having an internal capacity of 30 mL. Then, 9.14 g of a 3 wt % solution of PFB in R225 was added as a polymerization initiator. The interior of the system was freeze-deaerated, and then the reactor was sealed, followed by polymerization for 18 hours in a constant temperature shaking bath (20° C.). After the polymerization, the reaction solution was diluted with R225 and dropped into hexane to reprecipitate the polymer, followed by vacuum drying at 100° C. for 16 hours. As a result, 1.65 g of a non-crystalline polymer having fluorinated cyclic structures in its main chain (hereinafter referred to as the polymer 4A), was obtained. The molecular weight measured by GPC employing THF as a solvent and calculated as PSt, was such that the number average molecular weight (Mn) was 8,800, the weight average molecular weight (Mw) was 13,400, and Mw/Mn=1.53. Tg measured by the differential scanning calorimetery (DSC) was 115° C., and the polymer was a white powder at room temperature. The polymer obtained was soluble in acetone, THF, methanol and R225.

Example 6

Into a 200 mL glass reactor, 4 g of the polymer obtained in Example 4, 2.7 g of a 6.6 wt % methanol solution of sodium hydroxide and 80 g of methanol were put and stirred at room temperature for 20 hours. The reaction solution was concentrated by an evaporator and then dissolved in 120 g of dehydrated THF. Then, 0.38 g of chloromethyl methyl ether was added thereto, and the mixture was stirred at room temperature for 90 hours. The reaction solution was subjected to filtration through celite, and concentrated by an evaporator. The concentrated product was dissolved in R225 and washed with water, followed by liquid separation. The R225 layer was dropped into hexane to reprecipitate the polymer, followed by vacuum drying at 110° C. for 16 hours. As a result, 3.3 g of a non-crystalline polymer having fluorinated cyclic structures in its main chain (hereinafter referred to as the polymer 5A), was obtained. By analysis of $^{19}$F-NMR and $^1$H-NMR, it was confirmed that the methoxymethylation ratio was 32 mol %. Its molecular weight measured by GPC employing THF as a solvent and calculated as PSt, was such that the number average molecular weight (Mn) was 15,800, the weight average molecular weight (Mw) was 25,900, and Mw/Mn=1.64. Tg measured by the differential scanning calorimetery (DSC) was 111° C., and the polymer was a white powder at room temperature. The polymer obtained was soluble in acetone, THF, methanol and R225.

Examples 7 to 11

Measurement of Transparency in a Vacuum Ultraviolet Region of 157 nm 1 g of each of polymers 1A to 5A prepared in Examples 2 to 6 was dissolved in 10 g of propylene glycol monomethyl ether acetate and filtered through a filter made of PTFE having a pore diameter of 0.2 μm. The above prepared solution was applied on a CaF substrate by using a spin coater at 1,000 rpm at room temperature. After coating the CaF substrate, baking was carried out at 100° C. for 15 minutes to form a coating film having a thickness of 0.15 μm. Transmission spectra of such samples in 157 nm were measured. Transmittance (%) in 157 nm was shown in Table 1. The measuring apparatus used herein is as follows.

KV-201AD type extreme ultraviolet spectroscopic system (spectrometer)
wavelength region: 120 to 300 nm
Resolution: 1 to 4 nm

TABLE 1

|  | Polymer | Transmittance of light of 157 nm |
|---|---|---|
| Example 7 | 1A | 90 |
| Example 8 | 2A | 93 |
| Example 9 | 3A | 93 |
| Example 10 | 4A | 95 |
| Example 11 | 5A | 90 |

Examples 12 to 13

Measurement of Solubility in an Alkali Developer 1 g of each of polymers 3A and 5A prepared in Examples 4 and 6 was dissolved in 10 g of propylene glycol monomethyl ether acetate and filtered through a filter made of PTFE having a pore diameter of 0.2 μm, and the filtrate was applied on a silicon substrate. 2.38% of a tetramethyl ammonium hydroxide aqueous solution was dropped on a silicon substrate coated with a polymer, and the solubility was evaluated. The results are shown in Table 2.

TABLE 2

|  | Polymer | Solubility in an alkali developer |
|---|---|---|
| Example 12 | 3A | Dissolved |
| Example 13 | 5A | Not dissolved |

Example 14

2 g of the monomer obtained in Example 1 and 2.67 g of ethyl acetate were charged into a pressure resistant reactor made of glass and having an internal capacity of 30 mL. Then, 0.076 of IPP (diisopropyl peroxy dicarbonate) was added as a polymerization initiator. The interior of the system was freeze-deaerated, and then the reactor was sealed, followed by polymerization for 19 hours in a constant temperature shaking bath (40° C.). After the polymerization, the reaction solution was dropped into hexane to reprecipitate the polymer, followed by vacuum drying at 100° C. for 21 hours. As a result, 1.37 g of a non-crystalline polymer having fluorinated cyclic structures in its main chain (hereinafter referred to as the polymer 6A) was obtained. The molecular weight measured by GPC employing THF as a solvent and calculated as PSt, was such that the number average molecular weight (Mn) was 5,700, the weight average molecular weight (Mw) was 10,500, and Mw/Mn=1.84. The polymer was a white powder at room temperature. The polymer obtained was soluble in acetone, THF, methanol and R225.

Examples 15 and 16

1 g of each of polymers 3A and 6A prepared in Examples 4 and 14 was dissolved in 9 g of PGMEA (propylene glycol monomethyl ether acetate) and filtered through a filter made of PTFE having a pore diameter of 0.2 μm to obtain a composition for a resist protective film.

A silicon substrate was spin-coated with the above composition for a resist protective film, followed by heat treatment at 100° C. for 90 seconds to form a resist protective film having a thickness of 0.21 μm. Transmittance of light and contact angle against water of the resist protective film thus obtained are shown in Table 3.

TABLE 3

|  | Polymer | Transmittance of light of 193 nm (%) | Contact angle (°) |
|---|---|---|---|
| Example 15 | 3A | 99.3 | 74 |
| Example 16 | 6A | 98.5 | 74 |

Examples 17 and 18

Measurement of Solubility in an Alkali Developer 1 g of each of polymers 3A and 6A prepared in Examples 4 and 14 was dissolved in 9 g of PGMEA (propylene glycol monomethyl ether acetate) and filtered through a filter made of PTFE having a pore diameter of 0.2 μm, and the filtrate was applied on a silicon substrate. A silicon substrate coated with the polymer was immersed in 2.38% of a tetramethyl ammonium hydroxide aqueous solution or ultra pure water for 30 seconds to evaluate the solubility. The results are shown in Table 4.

TABLE 4

|  | Polymer | Solubility in an alkali developer | Solubility in ultrapure water |
|---|---|---|---|
| Example 17 | 3A | Dissolved | Not dissolved |
| Example 18 | 6A | Dissolved | Not dissolved |

INDUSTRIAL APPLICABILITY

The fluoropolymer of the present invention is applicable to ion exchange resins, ion exchange membranes, fuel cells, various cell materials, optical fibers, electronic members, transparent film materials, agricultural polyvinyl chloride films, adhesives, fiber materials, weather-resistant coating materials or the like, in addition to the use as a base polymer for photoresists and resist protective films.

The entire disclosures of Japanese Patent Application No. 2003-372654 filed on Oct. 31, 2003, Japanese Patent Application No. 2004-032038 filed on Feb. 9, 2004 and Japanese Patent Application No. 2004-185091 filed on Jun. 23, 2004 including specifications, claims and summaries are incorporated herein by reference in their entireties.

What is claimed is:

1. A fluorinated diene represented by the following formula (1):

$$CF_2=CFCH_2CH(C(R^1)(R^2)(OH))CH_2CH=CH_2 \quad (1)$$

wherein each of $R^1$ and $R^2$ which are independent of each other, is a fluorine atom or a fluoroalkyl group having at most 5 carbon atoms.

2. The fluorinated diene according to claim 1, wherein $R^1$ and $R^2$ are trifluoromethyl groups.

3. The fluorinated diene according to claim 1, wherein $R^1$ and $R^2$ are fluorine atoms.

4. The fluorinated diene according to claim 1, wherein $R^1$ is a trifluoromethyl group and $R^2$ is a fluorine atom.

5. The fluorinated diene according to claim 1, wherein $R^1$ is a trifluoromethyl group and $R^2$ is a pentafluoroethyl group.

6. The fluorinated diene according to claim 1, wherein $R^1$ and $R^2$ are pentafluoroethyl groups.

7. The fluorinated diene according to claim 1, wherein $R^1$ is a trifluoromethyl group and $R^2$ is a $C_5F_{11}$ group.

8. The fluorinated diene according to claim 1, wherein $R^1$ and $R^2$ are $C_5F_{11}$ groups.

9. A fluoropolymer (A) having monomer units formed by cyclopolymerization of the fluorinated diene as defined in claim 1.

10. A composition for a resist protective film, comprising the fluoropolymer (A) as defined in claim 9, and a solvent for dissolving or dispersing the fluoropolymer (A).

11. The composition for a resist protective film according to claim 10, which additionally contains an acid-generating compound (B) which generates an acid under irradiation with light.

12. The fluoropolymer (A) according to claim 9, wherein a proportion of hydroxyl groups of said monomer units have been blocked by a blocking group substituting the hydrogen atom of the hydroxyl groups.

13. The fluoropolymer (A) according to claim 12, wherein the proportion of blocked monomer units is 15-40 mol % based on the total of unblocked and blocked monomer units.

14. The fluoropolymer (A) according to claim 9, which also has monomer units derived from other radical polymerizable monomers.

15. A process for producing a fluoropolymer (A), comprising cyclopolymerization of the fluorinated diene as defined in claim 1.

* * * * *